US009999720B2

(12) United States Patent
Uhland et al.

(10) Patent No.: US 9,999,720 B2
(45) Date of Patent: Jun. 19, 2018

(54) DRUG RECONSTITUTION AND DELIVERY DEVICE AND METHODS

(71) Applicant: PALO ALTO RESEARCH CENTER INCORPORATED, Palo Alto, CA (US)

(72) Inventors: Scott A. Uhland, San Jose, CA (US); Felicia Linn, San Jose, CA (US); Michael I. Recht, Mountain View, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 1354 days.

(21) Appl. No.: 13/629,184

(22) Filed: Sep. 27, 2012

(65) Prior Publication Data

US 2014/0088486 A1 Mar. 27, 2014

(51) Int. Cl.
*A61M 37/00* (2006.01)
*A61M 31/00* (2006.01)
(Continued)

(52) U.S. Cl.
CPC .......... *A61M 5/14276* (2013.01); *A61M 5/19* (2013.01); *A61M 5/2448* (2013.01);
(Continued)

(58) Field of Classification Search
CPC ......... A61M 2005/14204; A61M 2005/14513; A61M 2005/3131; A61M 2005/2462;
(Continued)

(56) References Cited

U.S. PATENT DOCUMENTS 4,304,232 A 12/1981 Michaels
4,308,867 A 1/1982 Roseman et al.
(Continued)

FOREIGN PATENT DOCUMENTS

DE 4130843 A1 3/1993
WO 1994/01165 A1 1/1994
(Continued)

OTHER PUBLICATIONS

Fatakdawala, Hussain et al., "Hydrogen peroxide mediated transvaginal drug delivery," International Journal of Pharmaceutics 409 (2011) 121-127.
(Continued)

*Primary Examiner* — Nathan R Price
*Assistant Examiner* — Justin L Zamory
(74) *Attorney, Agent, or Firm* — Hollingsworth Davis, LLC

(57) ABSTRACT

Devices and methods are provided for drug delivery. The device may include a housing having a first compartment containing a drug in a dry, solid form, a second compartment containing a liquid carrier for the drug, and an expansion member located within or adjacent to the first or second compartment. The second compartment may be fluidly connectable to the first compartment by a rupturable barrier or mechanical valve. The device may also include an actuation system configured to expand the expansion member to rupture the rupturable barrier or open the mechanical valve and permit the liquid carrier to flow into the first compartment and mix with the drug to form a reconstituted drug solution.

27 Claims, 6 Drawing Sheets

(51) Int. Cl.
*A61M 5/00* (2006.01)
*A61M 5/142* (2006.01)
*A61M 5/19* (2006.01)
*A61M 5/24* (2006.01)
*A61M 5/145* (2006.01)

(52) U.S. Cl.
CPC .................. *A61M 5/14526* (2013.01); *A61M 2005/14513* (2013.01)

(58) Field of Classification Search
CPC .... A61M 2005/247; A61M 2005/2474; A61M 2005/287; A61M 5/2455; A61M 5/2459; A61M 5/2466; A61M 5/155; A61M 5/2066; A61M 5/2448; A61M 5/14593; A61M 5/14526; A61M 5/1409; A61M 5/1428; A61M 2039/0633; A61M 2039/066; A61M 2039/0666; A61K 9/0036

See application file for complete search history.

(56) References Cited

U.S. PATENT DOCUMENTS

| | | | |
|---|---|---|---|
| 4,402,695 A | | 9/1983 | Wong |
| 4,599,082 A | * | 7/1986 | Grimard ............... A61M 5/284 215/355 |
| 4,640,445 A | * | 2/1987 | Yamada ................ A61M 5/155 222/386.5 |
| 4,687,423 A | | 8/1987 | Maget et al. |
| 4,886,514 A | | 12/1989 | Maget |
| 4,902,278 A | | 2/1990 | Maget et al. |
| 5,002,540 A | | 3/1991 | Brodman et al. |
| 5,062,834 A | | 11/1991 | Gross et al. |
| 5,090,963 A | | 2/1992 | Gross et al. |
| 5,112,614 A | | 6/1992 | Magruder et al. |
| 5,135,499 A | | 8/1992 | Tafani et al. |
| 5,318,557 A | | 6/1994 | Gross |
| 5,354,264 A | | 10/1994 | Bae et al. |
| 5,415,629 A | | 5/1995 | Henley |
| 5,522,804 A | | 6/1996 | Lynn |
| 5,593,552 A | | 1/1997 | Joshi et al. |
| 5,780,058 A | | 7/1998 | Wong et al. |
| 5,816,248 A | | 10/1998 | Anderson et al. |
| 5,928,195 A | | 7/1999 | Malamud et al. |
| 5,951,538 A | | 9/1999 | Joshi |
| 6,030,375 A | | 2/2000 | Anderson et al. |
| 6,086,909 A | | 7/2000 | Harrison et al. |
| 6,139,538 A | | 10/2000 | Houghton et al. |
| 6,183,434 B1 | | 2/2001 | Eppstein |
| 6,322,532 B1 | | 11/2001 | D'Sa et al. |
| 6,352,524 B1 | | 3/2002 | Bunt et al. |
| 6,423,039 B1 | | 7/2002 | Rathbone et al. |
| 6,444,224 B1 | | 9/2002 | Rathbone et al. |
| 6,450,991 B1 | | 9/2002 | Bunt et al. |
| 6,461,334 B1 | * | 10/2002 | Buch-Rasmussen et al. ............................. 604/230 |
| 6,500,150 B1 | * | 12/2002 | Gross et al. ................. 604/131 |
| 6,532,386 B2 | | 3/2003 | Sun et al. |
| 6,591,133 B1 | | 7/2003 | Joshi |
| 6,638,246 B1 | | 10/2003 | Naimark et al. |
| 6,756,053 B2 | | 6/2004 | Zhang et al. |
| 6,776,164 B2 | | 8/2004 | Bunt et al. |
| 6,805,877 B2 | | 10/2004 | Massara et al. |
| 6,835,392 B2 | | 12/2004 | Hsu et al. |
| 6,962,579 B2 | | 11/2005 | Jellie |
| 6,978,172 B2 | | 12/2005 | Mori et al. |
| 7,004,171 B2 | | 2/2006 | Benita et al. |
| 7,083,590 B1 | | 8/2006 | Bunt et al. |
| 7,486,989 B2 | | 2/2009 | Sun et al. |
| 7,497,855 B2 | | 3/2009 | Ausiello et al. |
| 7,732,408 B2 | | 6/2010 | Josephson et al. |

| | | | |
|---|---|---|---|
| 2002/0010414 A1 | | 1/2002 | Coston et al. |
| 2002/0045883 A1 | | 4/2002 | Jellie |
| 2003/0018295 A1 | | 1/2003 | Henley et al. |
| 2003/0130558 A1 | | 7/2003 | Massara et al. |
| 2003/0219472 A1 | | 11/2003 | Pauletti et al. |
| 2004/0059388 A1 | | 3/2004 | Herbst et al. |
| 2004/0082937 A1 | | 4/2004 | Ausiello et al. |
| 2004/0087893 A1 | | 5/2004 | Kwon |
| 2004/0122359 A1 | * | 6/2004 | Wenz et al. .................... 604/82 |
| 2004/0219192 A1 | | 11/2004 | Horstmann et al. |
| 2005/0000514 A1 | | 1/2005 | Sullivan et al. |
| 2005/0054969 A1 | | 3/2005 | Hoff et al. |
| 2005/0124875 A1 | | 6/2005 | Kawano et al. |
| 2005/0244502 A1 | | 11/2005 | Mathias et al. |
| 2005/0267440 A1 | | 12/2005 | Herman et al. |
| 2006/0024358 A1 | | 2/2006 | Santini et al. |
| 2006/0184092 A1 | | 8/2006 | Atanasoska et al. |
| 2007/0038181 A1 | | 2/2007 | Melamud et al. |
| 2007/0225634 A1 | | 9/2007 | Ferren et al. |
| 2007/0269385 A1 | | 11/2007 | Yun et al. |
| 2008/0004564 A1 | | 1/2008 | Smith |
| 2008/0004596 A1 | | 1/2008 | Yun et al. |
| 2008/0262412 A1 | | 10/2008 | Atanasoska et al. |
| 2008/0269666 A1 | | 10/2008 | Wang et al. |
| 2009/0131737 A1 | | 5/2009 | Farren et al. |
| 2009/0171315 A1 | | 7/2009 | Versi |
| 2009/0281518 A1 | | 11/2009 | Grovender et al. |
| 2009/0306633 A1 | | 12/2009 | Trovato et al. |
| 2009/0308751 A1 | | 12/2009 | Evans et al. |
| 2010/0202246 A1 | * | 8/2010 | Huck et al. ................... 366/185 |
| 2011/0087155 A1 | | 4/2011 | Uhland et al. |
| 2011/0087192 A1 | * | 4/2011 | Uhland et al. ................ 604/514 |
| 2011/0087195 A1 | | 4/2011 | Uhland et al. |
| 2011/0092906 A1 | | 4/2011 | Boettger et al. |
| 2013/0211372 A1 | | 8/2013 | Rosenshein |

FOREIGN PATENT DOCUMENTS

| | | |
|---|---|---|
| WO | 1994/18952 A1 | 9/1994 |
| WO | 1997/41831 A1 | 11/1997 |
| WO | 2001/12101 A1 | 2/2001 |
| WO | 2005/056708 A2 | 6/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009/081411 A2 | 7/2009 |
| WO | 2010/048478 A2 | 4/2010 |

OTHER PUBLICATIONS

SáFILHO, O. G. et al., "Fixed-time artificial insemination with estradiol and progesterone for Bos indicus cows II: Strategies and factors affecting fertility," Science Direct, Theriogenology 72 (2009) 210-218.
Bridges, et al., "Timed-Artificial Insemination in Beef Cows: What are the Options?," Purdue University Cooperative Extension Service, West Lafayette, IN (REV Mar. 2008).
Hashimoto, et al., "Oxidative stress induces gastric epithelial permeability through claudin-3." Biochemical and Biophysical Research Communications (2008), vol. 376, pp. 154-157.
Seth, et al., "Probiotics ameliorate the hydrogen peroxide-induced epithelial barrier disruption by a PKC-and MAP kinase-dependent mechanism," Am J Physiol Gastrontest Liver Physiol (2008), vol. 294, pp. G1060-G1069. Retrieved from http://www.ajpgi.org on Jul. 28, 2009.
Kadajji, et al., "Water Soluble Polymers for Pharmaceutical Applications." Polymers (2011), vol. 3, pp. 1972-2009.
International Search Report and Written Opinion for PCT/US2013/051519 dated Jan. 7, 2014.
U.S. Appl. No. 13/629,124, Palo Alto Research Center Incorp.
U.S. Appl. No. 13/629,159, Palo Alto Research Center Incorp.

* cited by examiner

DRUG RECONSTITUTION AND DELIVERY DEVICE AND METHODS

FIELD

The present disclosure is generally in the field of drug delivery devices and methods, and more particularly to devices and methods for reconstituting and delivering drugs to human or animal subjects.

BACKGROUND

Drug delivery devices commonly store drug solutions on-board for delivery to patients. However, active drug formulations stored in solution often degrade quickly, losing potency and resulting in shortened device shelf-life. Drug solutions may also be prepared manually at the time of administration, requiring healthcare professionals to prepare and administer drug solutions to patients at specific times. Accordingly, it would be desirable to provide improved devices and methods to store, reconstitute, and deliver drug solutions to human or animal patients.

SUMMARY

In one aspect, a drug delivery device is provided. The device includes a housing having a first compartment containing a drug in a dry, solid form; a second compartment containing a liquid carrier for the drug; and an expansion member located within or adjacent to the first or second compartment. The second compartment is fluidly connectable to the first compartment by a rupturable barrier or mechanical valve. The device also includes an actuation system configured to expand the expansion member to facilitate mixing of the drug with the liquid excipient to form a reconstituted drug solution, to rupture the rupturable barrier or open the mechanical valve, and/or to drive release of the reconstituted drug solution out of the device. In one case, the actuation system is configured to expand the expansion member, first, to rupture the rupturable barrier or open the mechanical valve, and, then, to mix the liquid carrier with the drug. In another case, the rupturable barrier is ruptured or the mechanical valve is opened independently from expansion of the expansion member. In such a case, the expansion member is expanded to mix the liquid carrier with the drug and to expel the resulting reconstituted drug solution from the device after the rupturable barrier is ruptured or the mechanical valve is opened by a means other than expansion of the expansion member.

In another aspect, a method is provided for delivering a drug to a human or animal subject. The method includes (i) deploying a drug delivery device into the subject, wherein the drug delivery device includes a first compartment containing a drug in a dry, solid form, a second compartment containing a liquid carrier for the drug, and an expansion member; (ii) expanding the expansion member to rupture a rupturable barrier or open a mechanical valve, to mix the liquid carrier with the drug to form a reconstituted drug solution, and then (iii) releasing the reconstituted drug solution from the first and/or second compartment. In an alternative embodiment, the rupturable barrier is ruptured or the mechanical valve opened before the device is deployed into a subject. In that embodiment, the rupturing of the rupturable barrier or opening of the mechanical valve to place the first and second compartments in fluid communication with one another may occur in a separate step from the expanding of the expansion member.

DETAILED DESCRIPTION

The devices and methods described herein provide for the storage, reconstitution, and delivery of drug solutions. The devices, which generally are configured for in vivo deployment (i.e., implantation), are advantageously configured to separately store a drug in a dry, solid form and a liquid carrier for the drug, thereby allowing for improved shelf-life and drug potency. The devices also advantageously allow for in vivo reconstitution and delivery of the drug solution accordingly to a specific release timing profile.

Figure 1A:
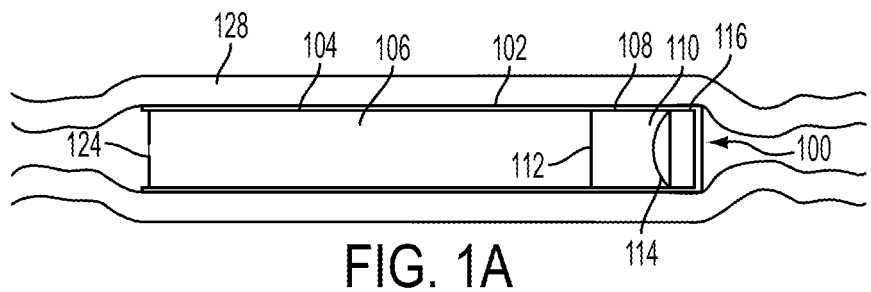
FIGS. 1A-1D are cross-sectional views, illustrating one embodiment of a drug delivery device having two compartments connectable by a rupturable barrier, and an expansion member, in a tissue lumen.

In one aspect, a device for drug delivery is provided. As shown in FIG. 1A, the device 100 has a housing 102 which includes a first compartment 104 containing a drug 106 in a dry, solid form and a second compartment 108 containing a liquid carrier 110 for the drug. The second compartment 108 is fluidly connectable to the first compartment 104 by a rupturable barrier or mechanical valve 112. The housing also includes an expansion member 114 located within or adjacent to the second compartment 108. Device 100 also includes an actuation system 116 configured to cause the expansion member to expand and rupture the rupturable barrier or open the mechanical valve 112 and thereby permit the liquid carrier 110 to flow into the first compartment 104 and mix with the drug 106 to form a reconstituted drug solution or suspension.

In another aspect, a method of delivering a drug is provided. The method may include (i) deploying a drug delivery device into a human or animal subject, where the drug delivery device has a first compartment containing a drug in a dry, solid form, a second compartment containing a liquid carrier for the drug, a rupturable barrier or mechanical valve between the first and second compartments, and an expansion member and actuation system; (ii) actuating the actuation system to cause the expansion member to expand and rupture the rupturable barrier or open the mechanical valve thereby fluidly connecting the first and second compartments; (iii) mixing the liquid carrier with the drug to form a reconstituted drug solution or suspension; and (iv) releasing the reconstituted drug solution or suspension from the first and/or second compartment.

Various embodiments and features of the drug delivery devices and methods are described in greater detail hereinafter.

Housing and Contents

The device includes a housing having at least a first compartment and a second compartment. The housing may be configured to facilitate deployment of the drug delivery device within a lumen of a human or animal subject. For example, the housing configuration may be based upon the particular lumenal site and human or animal anatomical considerations, for deployment with minimal discomfort to the patient. In certain embodiments, the device may be placed within the lumen by insertion into the lumen via an exterior body orifice. Accordingly, in certain embodiments, the housing is shaped and dimensioned to allow insertion and placement, i.e., deployment, of the device within the intended lumen via the exterior body orifice. For example, the housing may be shaped and dimensioned for the reproductive tract, such as for vaginal, cervical, or uterine insertion and placement, or for nasal, or rectal insertion and placement. As shown in FIGS. 1A-1D, the housing 102 may be an elongated, substantially cylindrical shape. For example, this configuration may be appropriate for vaginal device deployment in livestock, such as cattle, sheep, etc.

The materials of construction, size, shape, surface features, and other characteristics of the housing are configured such that the device can be deployed into the body of a patient, retained in the patient during operation of the device, and retrieved or recovered from the patient following operation of the device or when otherwise desired to be removed. For example, the device may be deployed until the drug formulation payload is depleted.

The housing may be formed of essentially any biocompatible material. Moreover, the housing material may be resistant to degradation in the mucosal environment of a tissue lumen or the gastrointestinal tract of a patient. Examples of suitable housing materials include stainless steel, titanium, and certain polymers. For example, the housing may be formed of polypropylene. The housing material may include a coating to enhance biocompatibility and/or operation of the device. For example, the housing may include a silicone coating on at least a part of the housing.

In the embodiment shown in FIG. 1A-D, two compartments are located within the housing. The first compartment 104 contains a drug 106 in a dry, solid form. For example, the drug 106 may be a lyophilized drug formulation. The second compartment 108 contains a liquid carrier for the drug 106 and is fluidly connectable to the first compartment 104 by a rupturable barrier or mechanical valve 112. For example, the rupturable barrier may include a breakable or dissolvable seal. In some embodiments, the second compartment contains a drug in a dry, solid form and the first compartment contains a liquid carrier for the drug.

The first and second compartments may be disposed within the housing such that they are adjacent to each other. The compartments may be sized to contain proportional volumes of drug and liquid carrier to create the desired composition of the drug solution or suspension. The compartments may also have a combined shape similar to that of the housing and be configured such that the compartments occupy a majority of the volume of the housing. In certain embodiments, the compartments are elongated and have a circular cross-sectional shape. Other cross-sectional shapes are also envisioned. The compartments may include a mixing structure, such as grooves in or raised fins or other features on the interior surfaces.

Figure 4A:
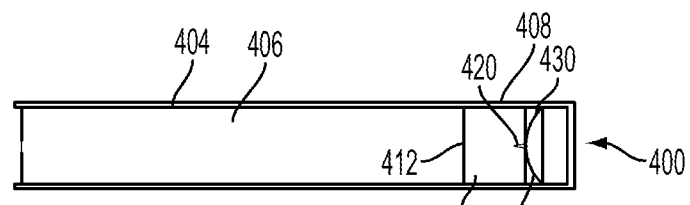
FIGS. 4A-4D are cross-sectional views, illustrating one embodiment of a drug delivery device having two compartments connectable by a rupturable barrier, and an expansion member having a spike member.
Figure 4B:
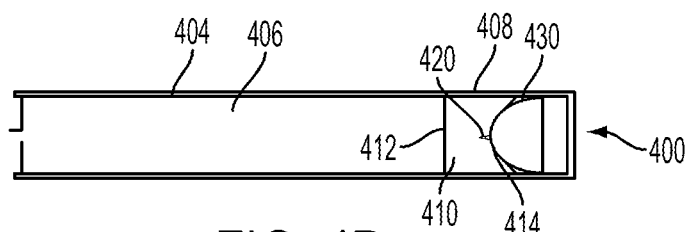
Figure 4C:
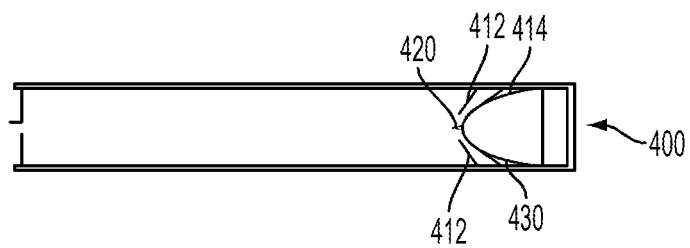
Figure 4D:
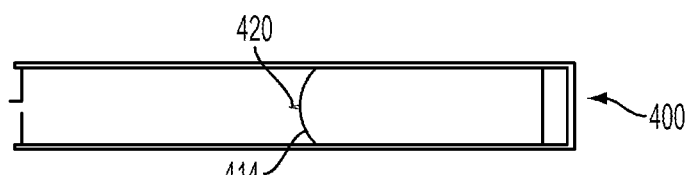
Figure 5A:
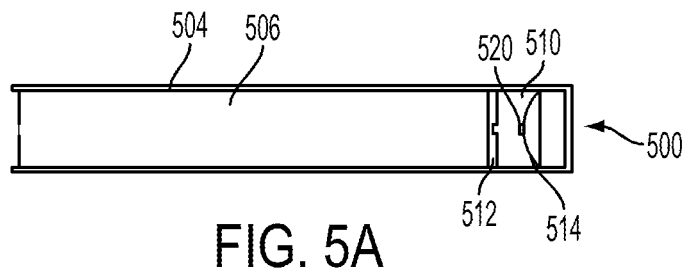
FIGS. 5A-5D are cross-sectional views, illustrating one embodiment of a drug delivery device having two compartments connectable by a mechanical valve, and an expansion member having a protrusion member.
Figure 5B:
Figure 5C:
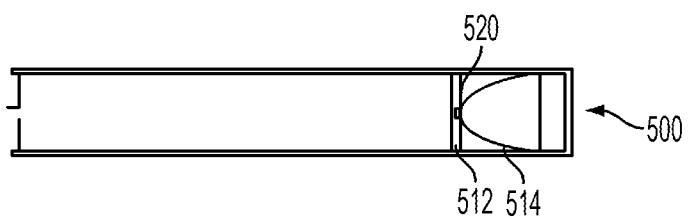
Figure 5D:
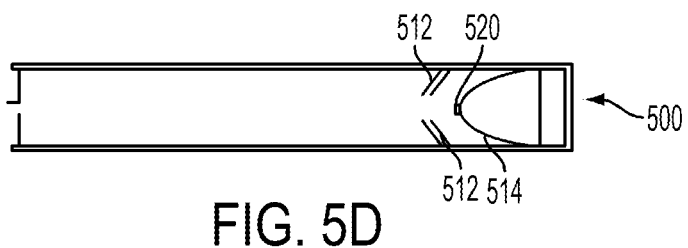

An expansion member 114 is located within or adjacent to the second compartment 108. In one embodiment, as shown in FIG. 1A, the expansion member 114 is located within the second compartment 108. In another embodiment, as shown in FIG. 4A, the expansion member 414 is located outside and adjacent the second compartment 408.

The housing may contain more than one expansion member, and more than one pair of first and second compartments. In addition or in the alternative, each pair of first and second compartments may include two or more expansion members that cooperate to rupture one or both of the compartments.

Figure 1B:
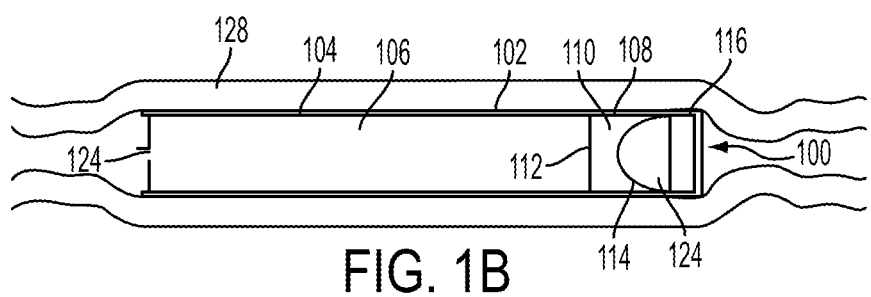
Figure 7:
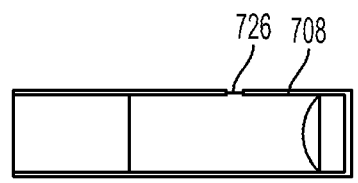
FIG. 7 is a cross-sectional view, illustrating one embodiment of a drug delivery device having two compartments connectable by a mechanical valve, and an expansion member.

The expansion member may be a balloon-like structure that expands or inflates to drive the liquid carrier into the first compartment and/or mix the liquid carrier and drug. For example, the expandable membrane may comprise a flexible, elastomeric sheet. Exemplary elastomeric sheets include polyester films. The expansion member is optionally coated with a metallized film on one or both surfaces for gas-tight sealing. In certain embodiments, the device is configured such that continued expansion of the expansion member causes the reconstituted drug solution or suspension to be expelled from the device via a release outlet in at least one of the first and second compartments. For example, the first and/or second compartments may include one or more release outlets therein. As shown in FIGS. 1A-1B, a single release outlet 124 may be included in the first compartment 104. As shown in FIG. 7, a release outlet 726 may be included in the second compartment 708.

The device also includes an actuation system operably connected to the expansion member. The actuation system may be included within the housing. The actuation system generally is configured to expand the expansion member to rupture the rupturable barrier and/or open the mechanical valve, which in turn permits the liquid carrier to flow into the first compartment and mix with the drug to form a reconstituted drug solution or suspension. The expandable membrane and/or mechanical valve may be operably connected to the actuation system. For example, the actuation system may be fluidly connected to the expandable membrane such that generation or release of a gas within the actuation system causes the swelling or expansion of the expansion member.

In one embodiment, the rupturable barrier includes a breakable or dissolvable seal. For example, as shown in FIG. 1A-1D, the rupturable barrier 112 may be a breakable seal that is configured to break upon application of a predetermined force from the expanding expansion member 114. Exemplary rupturable barriers include metallized films, polymer membranes, and combinations thereof. The rupturable barrier may also be configured to rupture upon application of a force from a manual process. For example, the rupturable barrier may be configured to break in response to a user-initiated process such as shaking the device, pressing a button, or pulling a tab immediately prior to implantation of the device in a human or animal subject. In such embodiments, the expansion member acts only to mix and dispense the reconstituted drug formulation. For example, the dry solid form of the drug may have sharp edges or may be formulated with excipient particles having sharp edges, where the sharp edges are effective to puncture the barrier upon a user vigorously shaking the device.

Alternatively, the rupturable barrier may include a degradable seal that dissolves, erodes, or otherwise degrades after a predetermined period of exposure to (contact with) the liquid carrier. The barrier may be configured such that the seal is weakened over time, but not ruptured until contacted by the expanding expansion member. The rupturable barrier may be configured to dissolve upon exposure to a specified condition such as high temperature, ultrasonic waves, or a certain light wavelength. For example, high temperature conditions may be provided by a heat source external to the device or housed on-board the device, such as an electrical resistor embedded in the barrier. For example, the barrier may be formed of a photomechanical or thermomechanical material that ruptures under specified light wavelengths or temperatures. For example, the barrier may be formed of a brittle material configured to crack or shatter when laser or acoustic (e.g., ultrasonic) energy is applied to it. For example, the barrier may be formed of a metal film, such as a zinc film, configured to act as a sacrificial anode of a galvanic cell and at least partially corrode upon activation of a circuit containing the film. The barrier may also be a porous polymer coated with a metal film configured to at least partially corrode, thereby exposing the pores.

In another embodiment, the first and second compartments are separated by a mechanical valve. For example, the mechanical valve may include a diaphragm, a plunger, a one-way valve, a crack valve, a deformable wall, or a movable wall. The mechanical valve may be operably connected to the actuation system such that upon actuation, the mechanical valve is opened. Opening of the mechanical valve may be independent of the expansion of the expansion member. For example, as shown in FIG. 2A-2D, the mechanical valve 212 may be opened to allow the liquid carrier 210 to flow into the first compartment 204 and mix with drug 206, independently of the expansion of the expansion member 214. The actuation system may be configured to open the mechanical valve and simultaneously expand the expansion member to mix the drug and liquid carrier and/or drive the drug solution or suspension out of the compartments.

In one embodiment, as shown in FIGS. 3A-3D, the expansion member 314 includes a spike member 320 effective to puncture the rupturable barrier 312 upon expansion of the expansion member 314. The expansion member may also include multiple spike members. For example, the spike member may be formed of the same material as the expansion member. Alternatively, the spike member may be formed in a metallized film deposited on the expansion member. For example, the metallized film may include a concentration of metal deposits that form the spike member. In one embodiment, the expansion member is formed by sealing two material layers together and the spike member is created at the seal. For example, the spike member may only be formed in response to sufficient pressure within the expansion member. In one embodiment, the spike member is ferromagnetic and held in place by a magnet on the opposite surface of the expansion member.

In one embodiment, as shown in FIGS. 5A-5D, the expansion member 514 includes a protrusion member 520 effective to open the mechanical valve 512 upon expansion of the expansion member 514. For example, the protrusion member and mechanical valve may act as a key and lock, with the protrusion member effective to open the mechanical valve upon mating of the protrusion member and mechanical valve. For example, the mechanical valve may include a plug formed of a material that expands to a specified volume, thereby forming an opening in the valve, and be sized and shaped such that the plug's geometry prevents the plug from resealing the valve. For example, the plug may have a trapezoidal shape and expand when exposed to a specific condition such as pressure or temperature. Alternatively, the valve may include a plug that forms an opening in the valve, such as by a shape change, when electrically, optically, or magnetically initiated.

In certain embodiments, a release outlet may be included in a third compartment contained in the housing. For example, the third compartment may be empty and separated from the first and/or second compartment by a rupturable barrier or mechanical valve. The rupturable barrier or mechanical valve may be ruptured or opened to allow the drug and liquid carrier to flow into the third compartment. The third compartment may provide additional volume in which the drug solution may be mixed and reconstituted.

In certain embodiments, the interior surface(s) of the first and/or second compartments have a hydrophobic or hydrophilic coating. The selection of the coating may depend on the hydrophilicity of the drug solution or suspension or other characteristics of the drug or carrier fluid. For example, the coating may be designed to facilitate the flow of the drug solution or suspension within or out of the first and second compartments.

Figure 6:
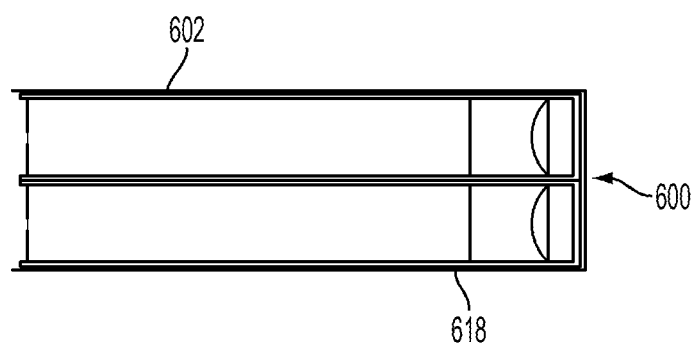
FIG. 6 is a cross-sectional view, illustrating one embodiment of a drug delivery device having two housings having two compartments and an expansion member.

The device may include more than one of the drug storage and reconstitution units described above. For example, as shown in FIG. 6, the device 600 may include a first housing 602 containing a first drug storage and reconstitution unit and a second housing 618 containing a second drug storage and reconstitution unit within the device. Each unit may have a first compartment and second compartment containing a drug in a dry, solid form and a liquid carrier for the drug, respectively. For example, a multi-unit device may be used to reconstitute and deliver a multiples doses of a drug solution or suspension (of the same drug or different drugs) to a human patient or animal subject over a dosing schedule, which may be predetermined or adjusted based on a sensor feedback or other considerations following in vivo deployment of the device. In one embodiment, the device may have two, three, or more of these housing units arranged in parallel and operable with separate or shared actuation system. This may further include a shared microcontroller, which may be on-board the device.

Actuation System

Figure 2A:
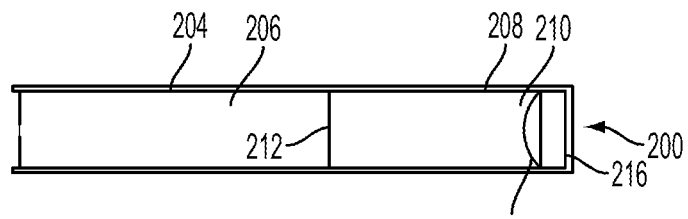
FIGS. 2A-2D are cross-sectional views, illustrating one embodiment of a drug delivery device having two compartments connectable by a mechanical valve, and an expansion member.
Figure 2B:
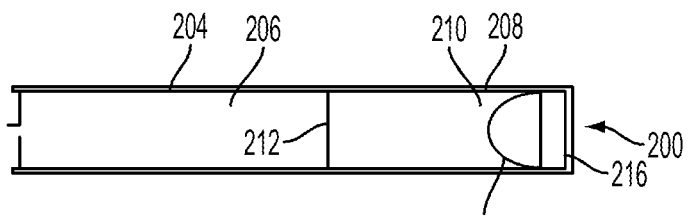
Figure 2C:
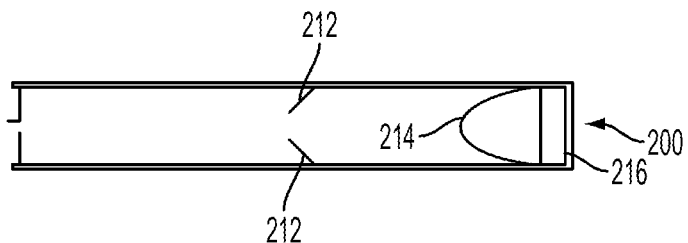
Figure 2D:
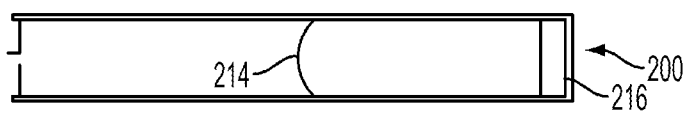
Figure 3A:
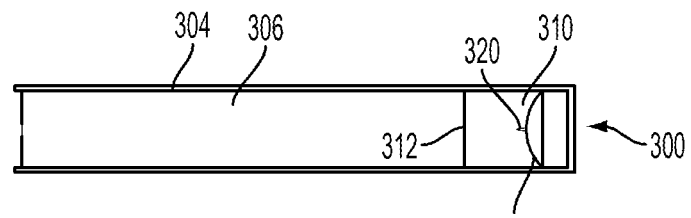
FIGS. 3A-3D are cross-sectional views, illustrating one embodiment of a drug delivery device having two compartments connectable by a rupturable barrier, and an expansion member having a spike member.
Figure 3B:
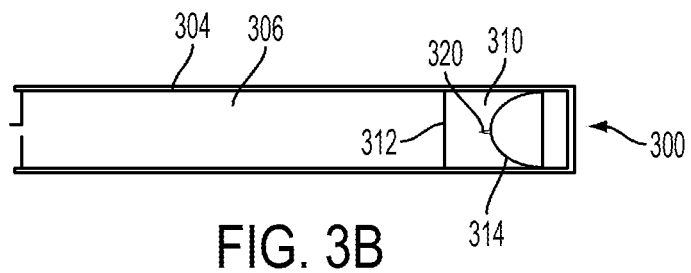
Figure 3C:
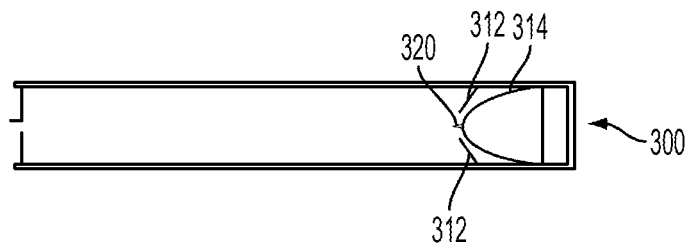
Figure 3D:
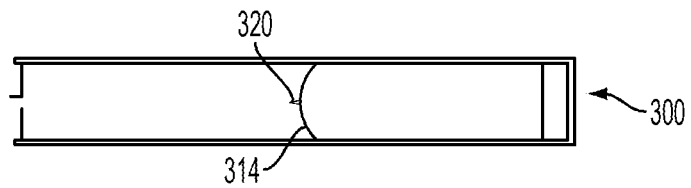

The device includes an actuation system which is configured to expand the expansion member to rupture the rupturable barrier or to open the mechanical valve, or to do both. For example, the expandable membrane and/or mechanical valve may be operably connected to the actuation system. The actuation system may also be operable to open one or more release outlets in the first and/or second compartments. In one embodiment, as shown in FIGS. 2C-2D, the actuation system 216 opens mechanical valve 212 and expands expansion member 214 simultaneously.

Generally, the actuation system is configured to expand the expansion member by an increase in pressure within and/or swelling of the expansion member or of a substance within the expansion member. In one embodiment, these may be triggered by generation of gas from a chemical reaction or release of a compressed gas from a containment vessel, within the actuation system. In another embodiment, the actuation system includes one or more mechanical or electromechanical displacement mechanisms, such as a spring or piezoelectric structure. The actuation system also may include one or more power sources, microcontrollers, microvalves, microcontainment vessels, and the like.

The power source may be any source of mechanical, electrical power or electromechanical power. The power source may include one or more batteries or fuel cells.

The microcontroller may be configured to control the actuation system of the device, and thereby control the timing of the opening of the mechanical valve and/or release outlet(s), the expansion of the expansion member, and the mixing and release of the drug solution. For example, the microcontroller may selectively transmit electrical or mechanical power to the actuation mechanism, expanding the expansion member, opening the mechanical valve, and/or opening the release outlet(s). The microcontroller may be configured to control the timing of reconstitution and delivery of the drug solution by applying the necessary electrical potentials to the actuation mechanism. The controller may be programmable or it may be pre-programmed to reconstitute and deliver the drug solution in accordance with a prescribed release schedule.

The actuation mechanism may include fluid-volume displacement, mechanical displacement, osmotic swelling displacement, electrostatically-induced compression, piezoelectric actuation, thermally/magnetically induced phase transformation, or combinations thereof, to expand the expansion member via positive displacement. Similarly, the actuation mechanism may be configured to open the mechanical valve and/or the release outlet(s) via similar mechanical, electrical, magnetic, pneumatic, or hydraulic forces.

Figure 1C:
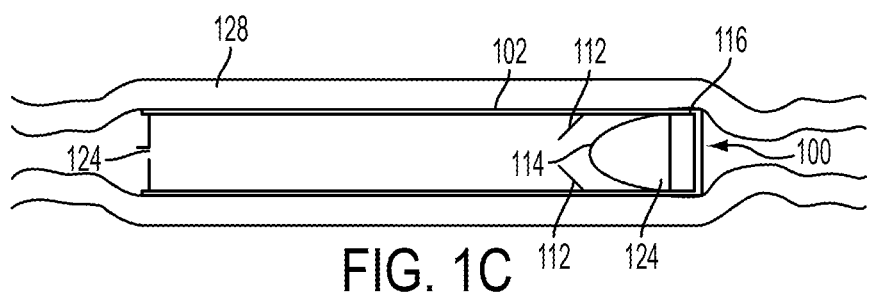
Figure 1D:
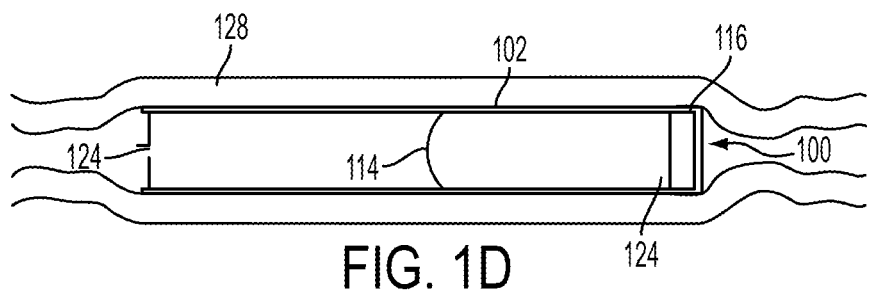

In certain embodiments, as shown in FIGS. 1B-1D, the actuation system 116 is configured to generate a displacement fluid 124 in operable communication with the expansion member 114 to expand the expansion member. For example, the expansion member may mix the liquid carrier and drug to constitute a drug solution and drive the drug solution out of the compartments via a positive displacement process. In certain embodiments, the actuation system is configured to expand and contract the expansion member to produce a mixing action. For example, the expansion member may be inflated, deflated, and reinflated to mix the liquid carrier and drug to reconstitute the drug solution.

In certain embodiments, the actuation system includes an electrochemical pump. The actuation system may include an electrolytic cell having a cathode and an anode which contact water or an aqueous solution to generate displacement a gas, such as oxygen, to drive the first and second drug formulations out of the first and second reservoirs, respectively.

In one embodiment, a channel is provided in the housing to allow aqueous secretions from the mucosal tissue of the lumen in which the device is deployed to contact the cathode and anode. In one embodiment, water or an aqueous solution is contained on-board the device. For example, the actuation system may include a reservoir containing an electrolytic solution, for example an ionic solution such as sodium nitrite. In one embodiment, the actuation system includes a reservoir containing deionized water and a solid electrolyte contacting the surfaces of the cathode and anode. For example, the solid electrolyte may be nafion, a sulfonated tetrafluoroethylene based fluoropolymer-copolymer, which also enables reversible electrolysis.

An electrical potential of about 1.0 V or greater may be applied to the electrodes of the electrolytic cell to generate oxygen at the anode. The reaction at the anode is described by EQ. 1. In the water, at the negatively charged cathode, a reduction reaction takes place, with electrons from the cathode being given to the hydrogen cations to form hydrogen gas as shown in EQ. 2. The pressure exerted by the generated oxygen and hydrogen causes the expansion member to expand through the compartments, thereby rupturing the rupturable barrier, opening the mechanical valve, mixing the liquid carrier and drug, and/or driving the reconstituted drug solution from the compartments.

The production of oxygen and hydrogen may be controlled by the power source and a microcontroller that is programmed to supply an electrical potential to the cathode and anode at a selected time.

$$2H_2O(l) \rightarrow O_2(g) + 4H^+(aq) + 4e^- \qquad \text{EQ. 1}$$

$$2H^+(aq) + 2e^- \rightarrow H_2(g) \qquad \text{EQ. 2}$$

In other embodiments, the actuation system is configured to expand the expansion member via positive displacement effectuated by the enlargement of a component within the actuation system, for example, a swellable material (such as a swellable gel) or an enlargeable repository. In some embodiments, the expansion member is expanded by osmotic swelling displacement. Optionally, one or more valves may be provided to selectively control the ingress of water into the repository or swellable material. For example, water from the lumen in which the device is deployed may be drawn into a repository or swellable material, causing the repository or swellable material to expand in volume. The expansion of the repository or swellable material may expand the expansion member. The actuation of the valve may be controlled by the microcontroller.

In other embodiments, the expansion member is expanded by an expansive force supplied by an induced phase transformation. For example, the actuation system may include an expandable repository containing a phase-transformable material. The phase-transformable material may be any liquid or solid that will undergo a phase transition from solid or liquid to gas when heated or subjected to an electromagnetic field. When the material transforms to a gas, the material expands, thereby expanding the expansion member. The actuation of the phase-transformation may be controlled by the microcontroller.

In other embodiments, the expansion member is expanded by electrostatically-induced compression or using a piezoelectric actuator. For example, a dielectric elastomeric actuator or piezoelectric actuator may be arranged such that a change in voltage or current to the actuator causes the actuator to exert a compressive force on the expansion member. The actuation of the actuator may be controlled by the microcontroller.

In other embodiments, positive displacement of the expansion member is achieved by mechanical displacement. For example, the mechanical displacement may involve a piston or a spring.

In certain embodiments, the actuation system further includes a wireless receiver for receiving wireless control signals from a separate, detached transmitting device. The device may be deployed into the patient by the patient, physician, veterinarian, or the like, and thereafter, the patient, physician, veterinarian, or the like, may actuate the release of the drug formulations using the transmitting device to transmit control signals to the deployed device. Furthermore, in some embodiments, the receiver and transmitting device may both be transceivers capable of transmitting and receiving control signals and other communications from each other. Accordingly, in certain embodiments, the transceiver may transmit data relevant to the operation of the device, such as data regarding the actuation of the expansion member, mechanical valve, and/or release outlet(s), the amount of drug solution remaining in the reservoir, and the remaining battery charge, as well as data relevant to the deployment environment, such as data detected or measured by an integral sensor. In some embodiments, the actuation system may also be wirelessly powered.

In certain embodiments, the device is configured for wireless operation, e.g., following deployment in the human or animal subject. In such cases, the device includes appropriate telemetry components as known in the art. For example, actuation of the drug solution reconstitution and dispensing may be done from a remote controller, e.g., external to the human or animal subject. Generally, the telemetry (i.e., the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if stored, a storage device, such as a rechargeable battery or capacitor. In still another case, the device is both wirelessly powered and wirelessly controlled.

In some embodiments, the actuation system may further include one or more sensors for analyzing the environment around the device. For example, a sensor may be employed to detect the temperature or the presence of a drug-degrading enzyme in a lumen in which the device is deployed. In such embodiments, the microcontroller may be further configured to dispense the drug solution after the abatement of the drug-degrading enzyme is detected or other suitable environmental conditions are detected for drug delivery.

Drug Solutions and Suspensions

The devices and methods described herein advantageously allow for the separate storage of a drug in a dry, solid form in the first compartment and a liquid carrier for the drug in the second compartment. The drug and liquid carrier are combined to form a drug solution suspension to be administered to a human or animal subject, such as a patient. The term "drug solution or suspension" as used broadly to refer to essentially any heterogeneous or homogeneous fluid (flowable) combination of the drug and liquid carrier, including but not limited to liquid solutions, solid-liquid suspensions, colloids, emulsions, dispersions, or combinations thereof.

In certain embodiments, the drug is a lyophilized drug formulation. For example, the drug formulation may include biologically active molecules such as hormones, multivitamin formulations, nucleic acids, and peptide or protein drugs including, but not limited to, antibodies. The drug may be in the form of microparticles or nanoparticles. The microparticles or nanoparticles may be coated with the drug or embedded with the drug such that the drug diffuses out of the particle or the particle dissolves to release the drug when the particle is contacted with liquid. For example, the drug may be encased in crystallized salt microparticles or nanoparticles that dissolve to release the drug upon contact with liquid. The dry, solid form of the drug may be substantially pure or it may include one or more excipients known in the art. The dry, solid drug may be provided on a protrusion member within the first or second compartment to avoid incomplete suspension resulting from incomplete wetting of the surfaces within the compartment.

The liquid carrier can be essentially any pharmaceutically acceptable excipient appropriate for combining with the particular drug. The liquid carrier may be aqueous or non-aqueous. The liquid carrier may include sterile water. The liquid carrier may include an organic liquid, such as polyethylene glycol, propylene glycol, or a fixed oil. The liquid carrier may also include one or more excipients needed to facilitate the drug's mixing with the liquid carrier, release from the device, and subsequent administration to a tissue site in the human or animal subject. For example, the liquid carrier may include pH adjustors, surfactants, viscosity modifiers, etc.

The device may be used to deliver a battery of drug formulations for a combination therapy, prophylaxis, or for another specific treatment.

In embodiments, the drug includes one or more proteins, peptides, or prodrugs. In some embodiments, the drug delivery device may be used to administer hormones or steroids, including, but not limited to, follicle stimulating hormone, parathyroid hormone, luteinizing hormone, gonadotropin-releasing hormone (GnRH), estradiol, progesterone, melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, atrial-natriuretic peptide, calcitonin, cholecystokinin, corticotropin-releasing hormone, erythropoietin, gastrin, ghrelin, glucagon, growth hormone-releasing hormone, human chorionic gonadotropin, human placental lactogen, growth hormone, inhibin, insulin, insulin-like growth factor, leptin, melanocyte stimulating hormone, orexin, oxytocin, prolactin, relaxin, secretin, somatostatin, thrombopoietin, thyroid-stimulating hormone, thyrotropin-releasing hormone, cortisol, aldosterone, testosterone, dehydroepiandrosterone, androstenedione, dihydrotestosterone, estrone, estriol, calcitriol, calcidiol, prostaglandins, leukotrienes, prostacyclin, thromboxane, prolactin releasing hormone, lipotropin, brain natriuretic peptide, neuropeptide Y, histamine, endothelin, enkephalin, renin, and pancreatic polypeptide.

In some embodiments, the drug delivery device may be used to administer cytokine signaling molecules or immunomodulating agents that are used in cellular communication. These molecules commonly comprise proteins, peptides, or glycoproteins. Cytokine signaling molecules include, for example, the four $\alpha$-helix bundle family which includes the IL-2 subfamily (e.g., erythropoietin (EPO) and thrombopoietin (THPO)), the interferon (IFN) subfamily and the IL-10 subfamily. Cytokine signaling molecules also include the IL-1, IL-18, and IL-17 families.

In some embodiments, the drug delivery device may be used to administer drug solutions for pain management, including, but not limited to, corticosteroids, opioids, antidepressants, anticonvulsants (antiseizure medications), nonsteroidal anti-inflammatory drugs, COX2 inhibitors (e.g., rofecoxib and celecoxib), ticyclic antidepressants (e.g., amitriptyline), carbamazepine, gabapentin and pregabalin, codeine, oxycodone, hydrocodone, diamorphine, and pethidine.

In some embodiments, the drug delivery device may be used to administer cardiovascular drug solutions. Examples include B-type natriuretic peptide (BNP), atrial natriuretic peptide (ANP), atrial natriuretic factor (ANF), atrial natriuretic hormone (ANH), and atriopeptin. Cardiovascular drug formulations that may be administered by the device also include, for example, antiarrhythmic agents, such as Type I (sodium channel blockers), including quinidine, lidocaine, phenytoin, propafenone; Type II (beta blockers), including metoprolol; Type III (potassium channel blockers), including amiodarone, dofetilide, sotalol; Type IV (slow calcium channel blockers), including diltiazem, verapamil; Type V (cardiac glycosides), including adenosine and digoxin. Other cardiacvascular drug solutions that may be administered by the device include ACE inhibitors, such as, for example, captopril, enalapril, perindopril, ramipril; angiotensin II receptor antagonists, such as, for example, candesartan, eprosartan, irbesartan, losartan, telmisartan, valsartan; beta blocker; and calcium channel blocker.

In some embodiments, the drug solutions may include components that are degradable by the enzymes present in the fluid secreted by, or otherwise present in, the mucosal tissue. For example, certain amino acids present in drug solutions may be degraded by the enzymes present in fluid secreted by the mucosal tissue. Accordingly, the devices and methods described herein may further include one or more of the permeation enhancement mechanisms described in U.S. Patent Application Publications No. 2011/0087195, No. 2011/0087192, and No. 2011/087155, the disclosures of which are incorporated herein by reference in pertinent part. In some embodiments, the drug solutions may include components that are degradable by the acidic pH of the lumenal fluid.

Methods of Use

Methods are provided for storing, reconstituting, and delivering a drug solution or suspension to human and animal patients. The drug delivery devices may include any of the device features described herein and may be used for various medical and therapeutic applications. The methods include deploying a drug delivery device into a human or animal subject. For example, the subject may be a mammalian animal (e.g., cow, sheep, horse, pig, or dog). The methods include various medical and veterinary therapies, as well as animal husbandry applications. In some embodiments, the device may be implantable. For example, the device may be adapted to be deployed in a lumen of a subject. As illustrated in FIGS. 1A-1D, the drug delivery device 100 may be placed in a lumen 128. The drug delivery device may be held in place by frictional engagement between the mucosal tissue and the housing. The lumen may be a vagina, cervix, uterus, bladder, or rectum. The device may be adapted to contact essentially any mucosal tissue surface. The device may be placed in the lumen by inserting the device through an exterior orifice of the patient into the lumen. In some embodiments, the device may be in a form that may be orally administered for delivery of a drug via the mucosal tissue of the gastrointestinal tract.

As shown in FIGS. 1A-1D, the drug delivery device 100 includes a first compartment 104 containing a drug 106 in a dry, solid form, a second compartment 108 containing a liquid carrier 110 for the drug 106, and an expansion member 114. The second compartment 108 is fluidly connectable to the first compartment 104 by a rupturable barrier 112. After the drug delivery device 100 is deployed in lumen 128, the expansion member 114 is expanded to rupture the rupturable barrier 112. Once the barrier 112 is ruptured, the liquid carrier 110 is permitted to flow into the first compartment 104. The liquid carrier 110 is mixed with the drug 106 to form a reconstituted drug solution and the reconstituted drug solution is released from the first compartment 104 via outlet 124.

The rupturable barrier may also be configured to rupture upon application of a force from a manual process. For example, the rupturable barrier may be configured to break in response to a user-initiated process such as shaking the device, pressing a button, or pulling a tab prior to device implantation. In such embodiments, the expansion member acts only to mix and dispense the reconstituted drug formulation. For example, the drug may be in the form of sharp particles that puncture the barrier upon a user shaking the device.

The outlet 124 may be opened simultaneously with the expansion of expansion member 114. Alternatively, as shown in FIG. 2, the outlet 224 may be opened after reconstitution of the drug solution.

In other embodiments, as shown in FIGS. 2A-2D, the first compartment 204 of device 200 is fluidly connectable to the second compartment 208 by a mechanical valve 212. After the device 200 is deployed, actuation system 216 opens mechanical valve 212 and expands expansion member 21 to permit and encourage liquid carrier 210 to flow into the first compartment 204 and mix with drug 206.

In certain embodiments, the liquid carrier may flow from the second compartment into the first compartment via a pressure differential (e.g., the first compartment is stored in a vacuum or fluid was pumped out of the first compartment). In certain embodiments, the expansion of the expansion member at least partly drives the liquid carrier into the first compartment. The liquid carrier is mixed with the drug to form a reconstituted drug solution or suspension and the reconstituted drug solution or suspension is released from the first and/or second compartment.

For example, the actuation system may be configured to open the mechanical valve and expand the expansion member simultaneously or according to a specific timing schedule. In one embodiment, the actuation system is configured to open the mechanical valve to allow the liquid carrier to flow into the first compartment prior to the expansion of the expansion member, which is effective to mix the liquid carrier and drug as well as drive the reconstituted drug solution or suspension out of the compartments. In another embodiment, as shown in FIGS. 2C-2D, the actuation system 216 opens mechanical valve 212 and expands expansion member 214 simultaneously.

In one embodiment, the step of mixing the liquid carrier with the drug includes expanding and contracting the expansion member. For example, the expansion member may be inflated, deflated, and reinflated to mix the liquid carrier and drug to reconstitute the drug solution or suspension. In certain embodiments, the step of releasing the reconstituted drug solution or suspension involves expanding the expansion member into the first and/or second compartments to displace the reconstituted drug solution therein through at least one release outlet in at least one in the first and/or second compartments.

As shown in FIG. 7, a release outlet 726 may be included in the second compartment 708. For example, the release outlet may be included in the second compartment in embodiments in which the second compartment contains a drug in a dry, solid form and the first compartment contains a liquid carrier for the drug, such that the expansion member may act as a gating mechanism by blocking the outlet upon expansion and allowing the reconstituted drug formulation to exit the housing only after the expansion member is collapsed. For example, this may be advantageous to prevent dispensing of the drug prior to reconstitution or mixing.

FIGS. 3A-3D, 4A-4D, and 5A-5D illustrate embodiments of the methods described herein. For example, FIGS. 3A-3D show device 300 having an expansion member 314 including spike member 320. Upon actuation, expansion member 314 expands and causes spike member 320 to progress toward and rupture rupturable barrier 312, permitting the liquid carrier 310 to flow into the first compartment 304 and mix with the drug 306 to form a reconstituted drug solution. FIGS. 4A-4D show a device 400 in which the expansion member 414 is located outside and adjacent second compartment 408 so as to reduce contact between the expansion member 414 and the drug solution. Upon actuation, expansion member 414 is expanded within third compartment 430 such that spike member 420 ruptures rupturable barrier 412, permitting the liquid carrier 410 to flow into the first compartment 404 and mix with the drug 406 to form a reconstituted drug solution. FIGS. 5A-5D illustrate device 500 in which expansion member 514 includes protrusion member 520. Upon actuation, expansion member 514 expands, thereby causing protrusion member 520 to mate with mechanical valve 512, causing the valve 512 to open and permitting the liquid carrier 510 to flow into the first compartment 504 and mix with the drug 506 to form a reconstituted drug solution.

The drug delivery devices may include any of the device features described herein. For example, the device may include a microcontroller configured to control the actuation system, and thereby control the timing of the release of the drug solution. Additionally, the devices described herein may further include any of the drug delivery device features described in U.S. patent application Ser. No. 13/629,159, entitled "Multiple Reservoir Drug Delivery Device and Methods", now U.S. Pat. No. 9,005,108, and U.S. patent application Ser. No. 13/629,124, entitled "Single Channel, Multiple Drug Delivery Devices and Methods," which are filed concurrently herewith and the disclosures of which are incorporated herein by reference in their entirety.

It will be appreciated that various of the above-disclosed and other features and functions, or alternatives thereof, may be desirably combined into many other different devices, methods, or applications. Various presently unforeseen or unanticipated alternatives, modifications, variations, or improvements therein may be subsequently made by those skilled in the art which are also intended to be encompassed by the following claims.

We claim:

1. A drug delivery device comprising:
a housing configuration for implantation in a human or animal subject which comprises:
a first compartment containing a drug in a dry, solid form;
a second compartment containing a liquid carrier for the drug, the second compartment being fluidly connectable to the first compartment by a rupturable barrier or mechanical valve; and
an expansion member located within or adjacent to the first or second compartment, wherein the expansion member is a balloon structure comprising a flexible, elastomeric sheet; and
an actuation system configured to expand the expansion member to rupture the rupturable barrier or open the mechanical valve and to expand and contract the expansion member to produce a mixing action to permit the liquid carrier to flow into the first compartment and mix with the drug to form a reconstituted drug solution.

2. The device of claim 1, wherein the device is configured such that continued expansion of the expansion member causes the reconstituted drug solution to be expelled from the device via a release outlet in at least one of the first and second compartments.

3. The device of claim 1, wherein the actuation system is configured to generate a displacement fluid that expands the expansion member.

4. The device of claim 1, wherein the actuation system comprises an electrochemical pump.

5. The device of claim 1, wherein the rupturable barrier comprises a friable or dissolvable seal.

6. The device of claim 1, wherein the device is configured for intravaginal retention in the human or animal subject.

7. The device of claim 1, further comprising at least one additional housing.

8. The device of claim 1, wherein the expansion member comprises a protrusion member effective to open the mechanical valve upon expansion of the expansion member.

9. The device of claim 1, wherein the expansion member comprises a spike member effective to puncture the rupturable barrier upon expansion of the expansion member.

10. The device of claim 1, wherein the drug comprises a lyophilized drug formulation.

11. The device of claim 1, wherein an interior surface of the first and/or second compartments comprises a hydrophobic or hydrophilic coating.

12. The device of claim 1, wherein the liquid carrier comprises water and one or more pharmaceutically acceptable excipients.

13. A method of delivering a drug comprising:
deploying a drug delivery device into a human or animal subject, wherein the drug delivery device comprises a first compartment containing a drug in a dry, solid form and a second compartment containing a liquid carrier for the drug;
inflating an expandable membrane to rupture a rupturable barrier or open a mechanical valve to fluidly connect the first and second compartments;
mixing the liquid carrier with the drug to form a reconstituted drug solution, wherein the step of mixing the liquid carrier with the drug comprises expanding and contracting the expandable membrane; and
releasing the reconstituted drug solution from the first and/or second compartment.

14. The method of claim 13, wherein the drug comprises a lyophilized drug formulation.

15. The method of claim 13, wherein the step of releasing the reconstituted drug solution comprises inflating the expandable membrane to displace the reconstituted drug solution from the first and/or second compartments through at least one release outlet in at least one in the first and/or second compartments.

16. The method of claim 13, wherein the expansion member comprises a protrusion member effective to open the mechanical valve upon expansion of the expansion member.

17. The method of claim 13, wherein the expansion member comprises a spike member effective to puncture the rupturable barrier upon expansion of the expansion member.

18. The method of claim 13, wherein the drug delivery device is deployed into the human or animal subject intravaginally.

19. A drug delivery device comprising:
a first compartment containing a drug in a dry, solid form;
a second compartment containing a liquid carrier for the drug, the second compartment being fluidly connectable to the first compartment by a rupturable barrier;
an expansion member; and an actuation system configured to expand and contract the expansion member to mix the liquid carrier with the drug, after the rupturable barrier is ruptured, to form a reconstituted drug solution and expel the reconstituted drug solution from the device via a release outlet.

20. The device of claim 19, wherein the rupturable barrier comprises a material configured to degrade upon being heated to a specified temperature and/or exposed to light irradiation of a specified wavelength.

21. The device of claim 19, wherein the rupturable barrier comprises a material soluble in the liquid carrier.

22. A method of administering a drug to a human or animal subject, the method comprising:
providing a drug delivery device which comprises:
a first compartment containing a drug in a dry, solid form,
a second compartment containing a liquid carrier for the drug, and
an expansion member;
rupturing a rupturable barrier to place the first and second compartments in fluid communication with one another;
deploying the drug delivery device in the human or animal subject; and
controlling the expansion member to (i) expand and contract to facilitate mixing of the liquid carrier with the drug to form a reconstituted drug solution, and (ii) release the reconstituted drug solution from a release outlet of the device.

23. The method of claim 22, wherein the rupturing of the rupturable barrier is performed prior to the deployment of the drug delivery device in the human or animal subject.

24. The method of claim 23, wherein the step of rupturing the rupturable barrier comprises manually shaking the device.

25. The method of claim 24, wherein the drug comprises particles configured to puncture the rupturable barrier upon shaking.

26. The method of claim 22, wherein the rupturing of the rupturable barrier is performed after the deployment of the drug delivery device in the human or animal subject.

27. The method of claim 22, wherein the drug delivery device is deployed intravaginally in the human or animal subject.

* * * * *